(12) United States Patent
Milella, Jr. et al.

(10) Patent No.: US 11,691,255 B2
(45) Date of Patent: *Jul. 4, 2023

(54) ADJUSTABLE DISPOSABLE TORQUE LIMITING MOUNT AND DEVICE

(71) Applicant: ECA Medical Instruments, Inc., Newbury Park, CA (US)

(72) Inventors: Michael J. Milella, Jr., Thousand Oaks, CA (US); Gary Norsworthy, Newbury Park, CA (US)

(73) Assignee: ECA Medical Instruments, Inc., Thousand Oaks, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 16/968,571

(22) PCT Filed: Feb. 8, 2019

(86) PCT No.: PCT/US2019/017351
§ 371 (c)(1),
(2) Date: Aug. 8, 2020

(87) PCT Pub. No.: WO2019/157379
PCT Pub. Date: Aug. 15, 2019

(65) Prior Publication Data
US 2021/0039232 A1 Feb. 11, 2021

Related U.S. Application Data

(60) Provisional application No. 62/628,877, filed on Feb. 9, 2018.

(51) Int. Cl.
| | | |
|---|---|---|
| *B25B 23/142* | (2006.01) | |
| *B25B 13/08* | (2006.01) | |
| *B25B 23/14* | (2006.01) | |

(52) U.S. Cl.
CPC .......... *B25B 23/1427* (2013.01); *B25B 13/08* (2013.01); *B25B 23/141* (2013.01)

(58) Field of Classification Search
CPC .............. B25B 23/1427; B25B 23/141; B25B 23/0035; B25B 23/1422; B25B 13/08
(Continued)

(56) References Cited

U.S. PATENT DOCUMENTS

| | | | |
|---|---|---|---|
| 2,982,536 A | * | 5/1961 | Kordes ...................... F16F 1/40 267/153 |
| 4,403,531 A | | 9/1983 | Bailey |

(Continued)

OTHER PUBLICATIONS

Alwayse Engineering (https://web.archive.org/web/20161226221106/http://www.alwayse.co.uk/ball-transfer-units/spring-loaded-units/large-top-flange.html). (Year: 2016).*

*Primary Examiner* — Don M Anderson
*Assistant Examiner* — Robert C Moore
(74) *Attorney, Agent, or Firm* — Ferguson Case Orr Paterson LLP

(57) ABSTRACT

Disclosed are aspects of exemplars of torque-limiting devices, methods and mechanisms. Exemplary methods may include placing an actuator in a tool containment interface of a handle, the interface being fluidly connected to an adjustment interface and adjustable via a fixation fastener; movably mounting a tool portion with an actuation catch and a work piece engaging region (WER) in the interface; applying sufficient force to the movable mounting to the handle may be via pins, guides and slots. Said catch may be one of a body catch and a lever catch; and, the actuator terminates on one of a ball shaped end that forms an interface with the body catch and a force lever that forms an interface with the lever catch.

10 Claims, 10 Drawing Sheets

(58) Field of Classification Search
USPC .................. 81/467, 475, 478, 483; 73/862.21
See application file for complete search history.

(56) References Cited

U.S. PATENT DOCUMENTS

| | | | |
|---|---|---|---|
| 5,224,403 A | | 7/1993 | Rueb |
| 5,337,638 A | * | 8/1994 | Coss .................. B25B 23/1427 |
| | | | 173/176 |
| 6,021,694 A | * | 2/2000 | Beger ................ B25B 23/0035 |
| | | | 73/862.21 |
| 2007/0039432 A1 | | 2/2007 | Cutler |
| 2010/0147118 A1 | | 6/2010 | Hsieh |
| 2011/0132153 A1 | | 6/2011 | Teper |
| 2013/0068714 A1 | | 3/2013 | Sprainis |
| 2016/0059395 A1 | * | 3/2016 | Huguelet ............. B25B 23/141 |
| | | | 81/477 |
| 2016/0075005 A1 | * | 3/2016 | Hayes, Jr. ............ B25B 23/142 |
| | | | 81/186 |

\* cited by examiner

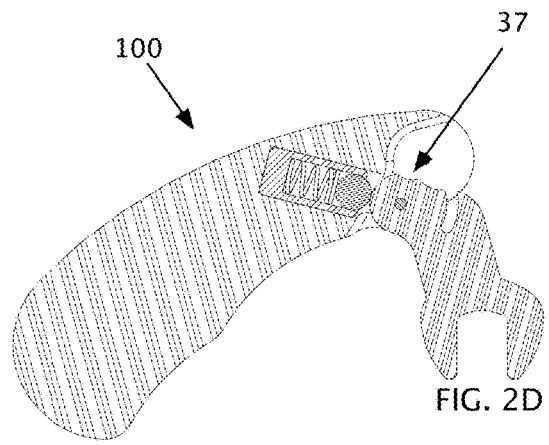
FIG. 2D
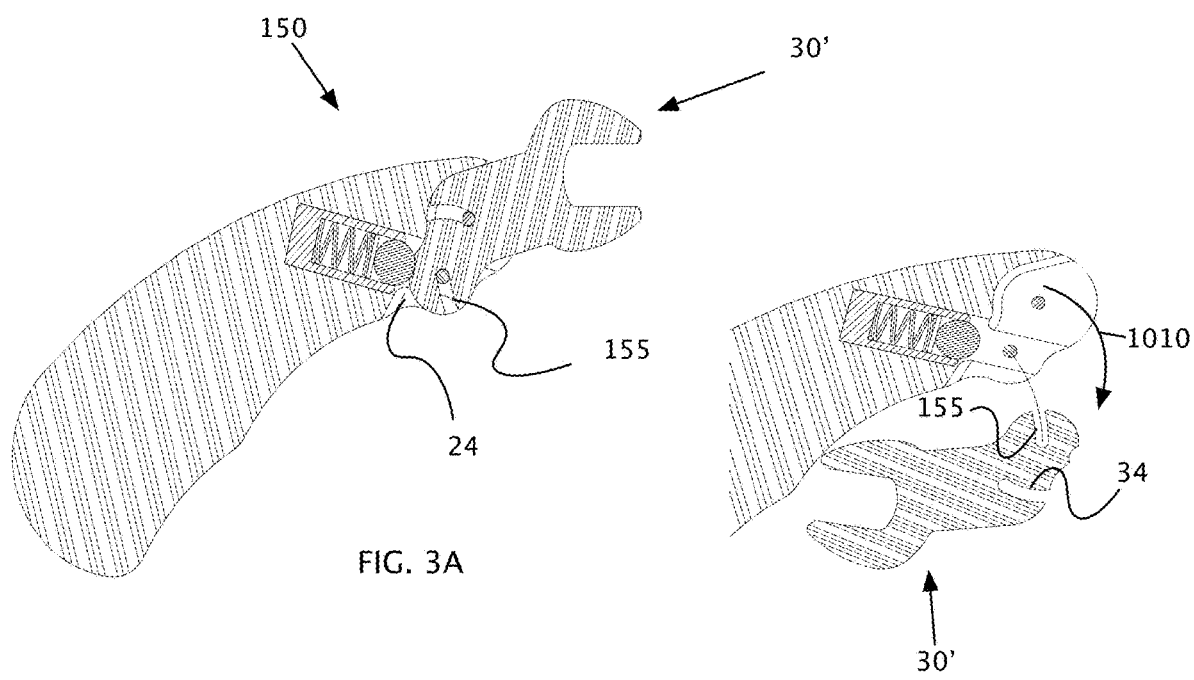
FIG. 3A
FIG. 3B

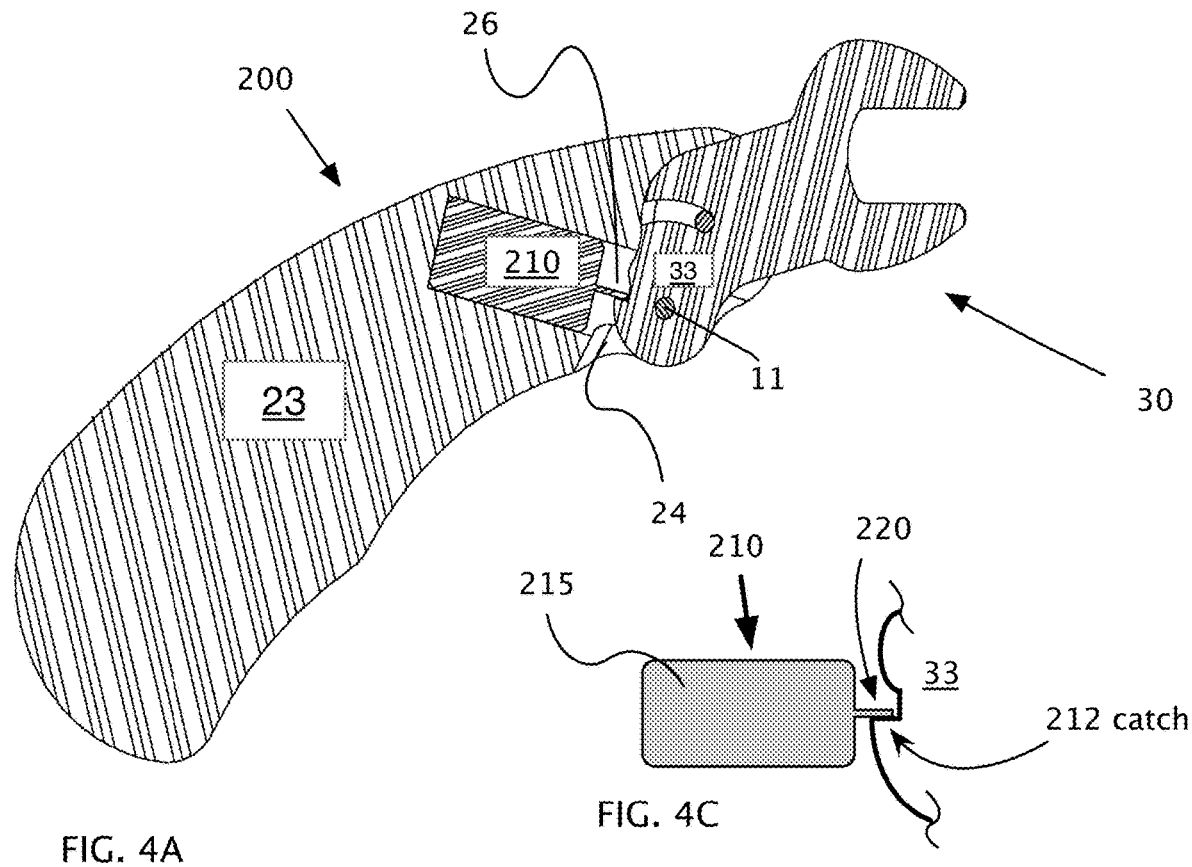
FIG. 4A
FIG. 4C
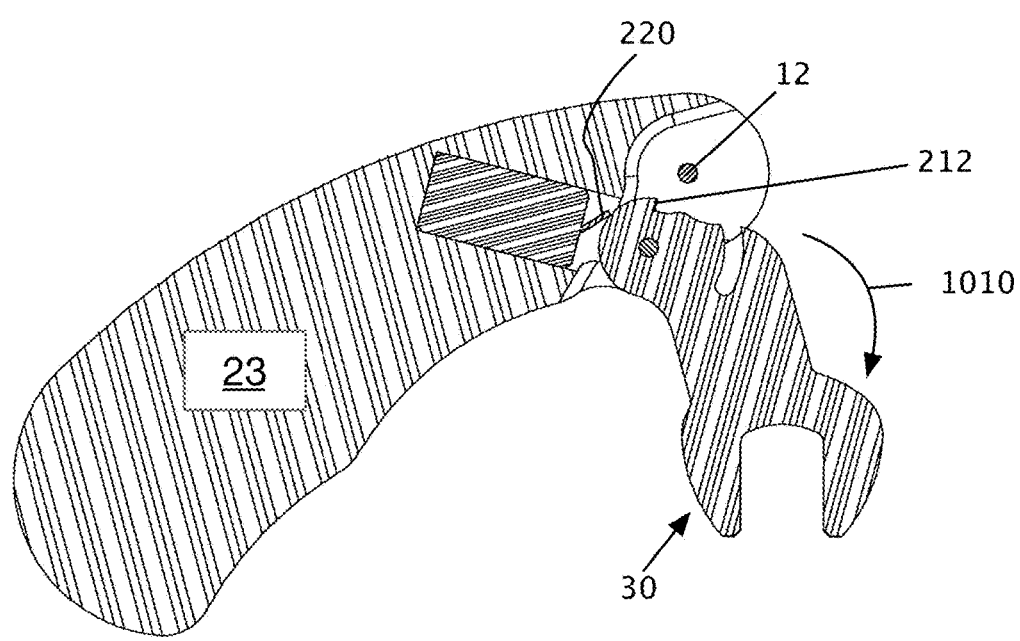
FIG. 4B

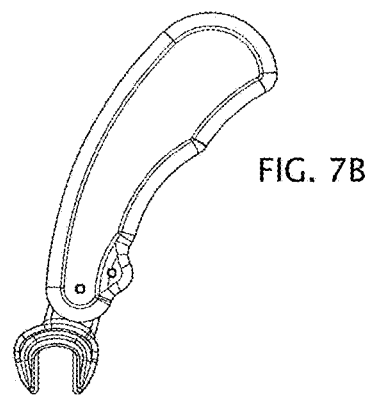
FIG. 7B
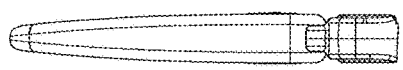
FIG. 7A
FIG. 7E
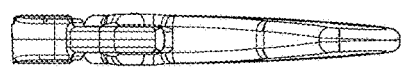
FIG. 7C
FIG. 7D
FIG. 7F

ADJUSTABLE DISPOSABLE TORQUE LIMITING MOUNT AND DEVICE

CROSS-REFERENCE TO RELATED APPLICATIONS

This is a national phase application of International Patent Application No. PCT/US19/17351 filed on Feb. 8, 2019, which claims the benefit of U.S. Provisional Patent Application No. 62/628,877 filed Feb. 9, 2018. The contents of each of these applications are incorporated by reference herein.

BACKGROUND

1. Field

This disclosure relates to unidirectional hand held disposable torque-limiting devices that are suitable for hand operation.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Reusable torque-limiting systems need to be sterilized between uses and typically must be serviced and recalibrated periodically to ensure performance within specifications. Disposable torque-limiting systems are an alternative to the reusable systems. Once the torque-limiting system has been used, it is discarded.

Thus there is a need for disposable unidirectional torque-limiting systems which operate in specification over a predetermined number of actuations. The disclosure is directed to these and other important needs.

DISCLOSURE

Aspects of exemplars of torque-limiting devices, methods and mechanisms are disclosed herein, in some exemplars a generally elongated handle with a tool containment interface formed on the front side of the handle provides one or more guides formed through the handle and a tool portion to movably attach the tool portion. An actuator is mounted in a containment; the containment is in fluid communication to an adjustment interface; the actuator has a ball shaped end such as a ball on a spring or a member with a ball shaped end. A tool portion configured to movable fit in at least part of the tool containment has a work piece engaging region (WER), an optional pin guide may be formed in the tool portion, an optional guide may be formed in the tool portion; a body catch forming an interface for a ball shaped end of the actuator; a pin configured to fit snugly in the pin guide thereby pivotally attaching the tool portion; optionally a pin may be added which is configured to fit loosely in the guide slot; a fixation fastener is mounted in the adjustment interface to adjust the depth (or height) of the and, wherein when sufficient force is applied to the actuator the body catch disengages the ball end and the tool portion is released.

In some instances a containment with an annular wall and a closed end is formed in the handle to mount the actuator to the handle. In some instances the actuator further comprising a generally cylindrical housing with an open end and an end portion closing off the cylinder; a spring resting against the end portion; and, a ball fitted into the housing and extending into the body catch. In some instances the spring has a predetermined compressive force limit. In some instances the tool portion has a retention slot in place of the second pin guides; and, the tool portion may be removed from the tool containment by rotating it off the first and second pins.

In some exemplars the actuator further comprising an actuation body and a elastomeric bushing configured to cause a ball shaped nose of the actuation body to apply a predetermined amount of force to the body catch. In some instances the bushing has a diameter less than the diameter inside the containment. In some instances the bushing fits into a well 29' to configured to retain it and allowing volume around the bushing for expansion which will occur during compression by the application of force to the ball shaped nose.

In some exemplars the actuator the actuator further comprising an actuation body and an elastomeric bushing configured to cause a ball shaped nose of the actuation body to apply a predetermined amount of force to the body catch. In some instances the containment is an annular wall of the containment has a bushing expansion region of the annular wall which is of a greater diameter inside the containment to allow volume around the bushing for bushing expansion which will occur during compression by the application of force to the ball shaped nose.

Aspects of exemplars of torque-limiting devices, methods and mechanisms are disclosed herein, in some exemplars a generally elongated handle with a tool containment interface formed on the front side of the handle provides a first pin guide and a third pin guide formed through the handle to movably attach a tool portion. An actuator is mounted in the handle; a tool portion configured to movably fit in at least part of the tool containment comprising; a work piece engaging region; a second pin guide formed in the tool portion; a guide slot formed in the tool portion; a lever catch forming an interface for force lever end of the actuator; a first pin configured to fit snugly in the first pin guide; a second pin configured to fit loosely in the guide slot; and, wherein when sufficient force is applied to the actuator the body catch disengages the fore lever from the lever catch and the tool portion is released.

In some instances a containment with an annular wall and a closed end is formed in the handle to mount the actuator to the handle. In some instances the force lever is frangible.

Aspects of exemplars of torque-limiting devices, methods and mechanisms are disclosed herein, in some exemplars the method comprises placing an actuator in a tool containment interface of a handle; movable mounting a tool portion with an actuation catch and a work piece engaging region (WER) in the interface; adjusting the depth a fixation fastener within an adjustment interface in the handle and which is also fluidly connected to the containment; wherein the adjustment changes the force the actuator applies to the tool portion; and, applying sufficient force to disengage the tool portion from the torque limiting actuator. The movable mounting to the handle may be via pins, guides and slots. Said catch is one of a body catch and a lever catch; and, the actuator terminates on one of a ball shaped end that forms and interface with the body catch and a force lever that forms an interface with the lever catch.

DRAWINGS

The above-mentioned features of the present disclosure will become more apparent with reference to the following description taken in conjunction with the accompanying drawings wherein like reference numerals denote like elements. In addition, the drawings are not necessarily drawn to scale. In the drawings:

FIG. 2D shows a cut away view of the FIG. 2A asymmetrical disposable torque limiting device in an actuated configuration.

FIGS. 3A and 3B show aspects of a removable tool exemplary for an asymmetrical disposable torque limiting device.

FIGS. 4A and 4B show cut away views an asymmetrical disposable torque limiting device in an unactuated and actuated configuration.

FIG. 4C shows aspects of a torque limiting lever actuator shown in FIG. 4A.

FIG. 7A shows a top view of an asymmetrical disposable torque limiting device.

FIG. 7B shows a left side view of an asymmetrical disposable torque limiting device.

FIG. 7C shows a bottom view of an asymmetrical disposable torque limiting device.

FIG. 7D shows a right side view of an asymmetrical disposable torque limiting device.

FIG. 7E shows a front side view of an asymmetrical disposable torque limiting device.

FIG. 7F shows a back side view of an asymmetrical disposable torque limiting device.

As shall be appreciated by those having ordinary skill in the art, the figures are not to scale, and modifications to scale within a figure or across the figures are considered within the present disclosure. All callouts in Figures are hereby incorporated by this reference as if fully set forth herein.

FURTHER DISCLOSURE

Aspects of asymmetrical disposable torque limiting devices are provided in exemplary implementations of this disclosure. Those of ordinary skill in the art will recognize small design variations that are within the scope of this disclosure. The identification of some aspects and not others shall not be considered limiting in the disclosure but may be limitations in claims.

FIGS. 1A-7F illustrate aspects of implementations of the asymmetrical disposable torque limiting device (ADTLD) which may support a plethora of tools such as drivers, wrenches, closed sockets, and the like.

Figure 1A:
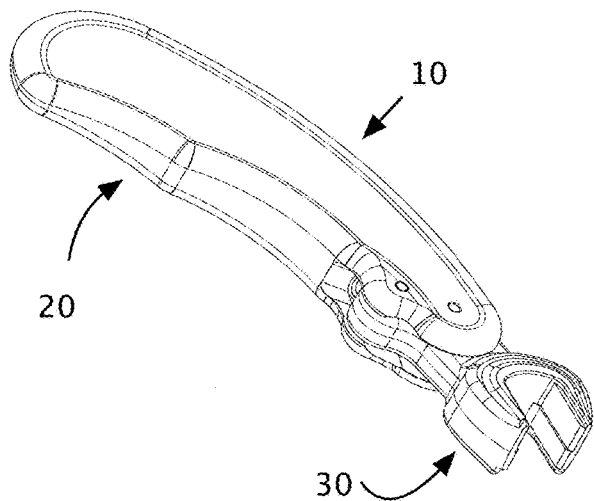
FIGS. 1A, 1B and 1C show external views of aspects of asymmetrical disposable torque limiting devices in unactuated and fully actuated positions.
Figure 1B:
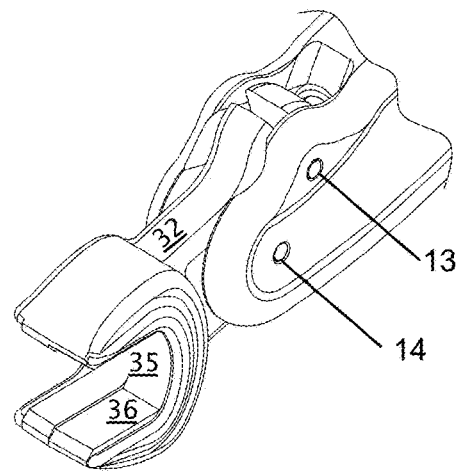
Figure 1C:
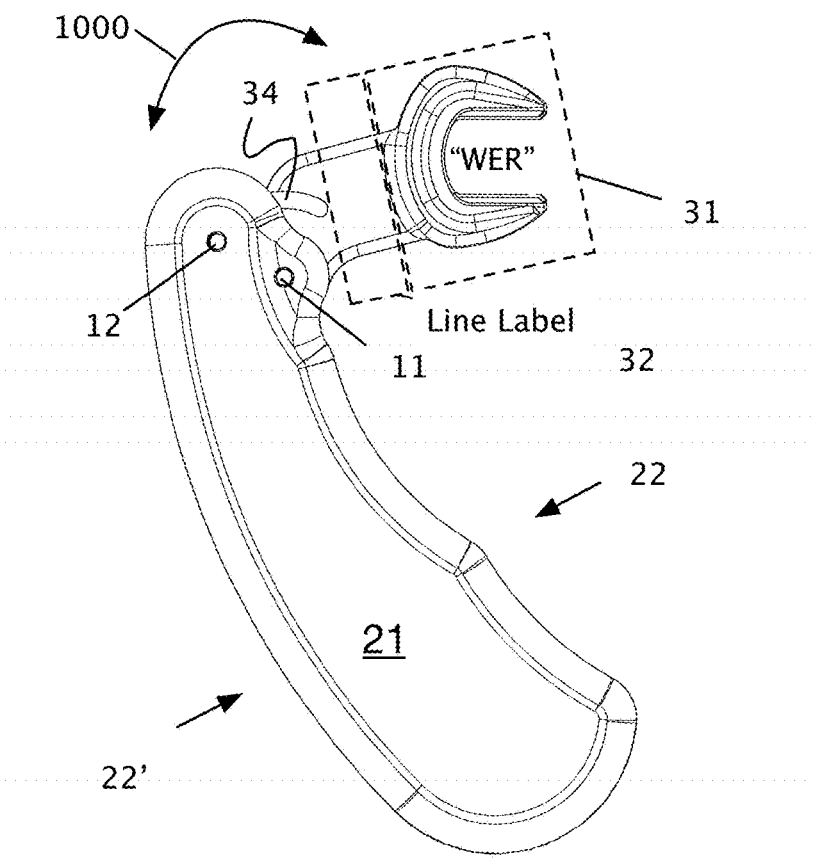
Figure 2A:
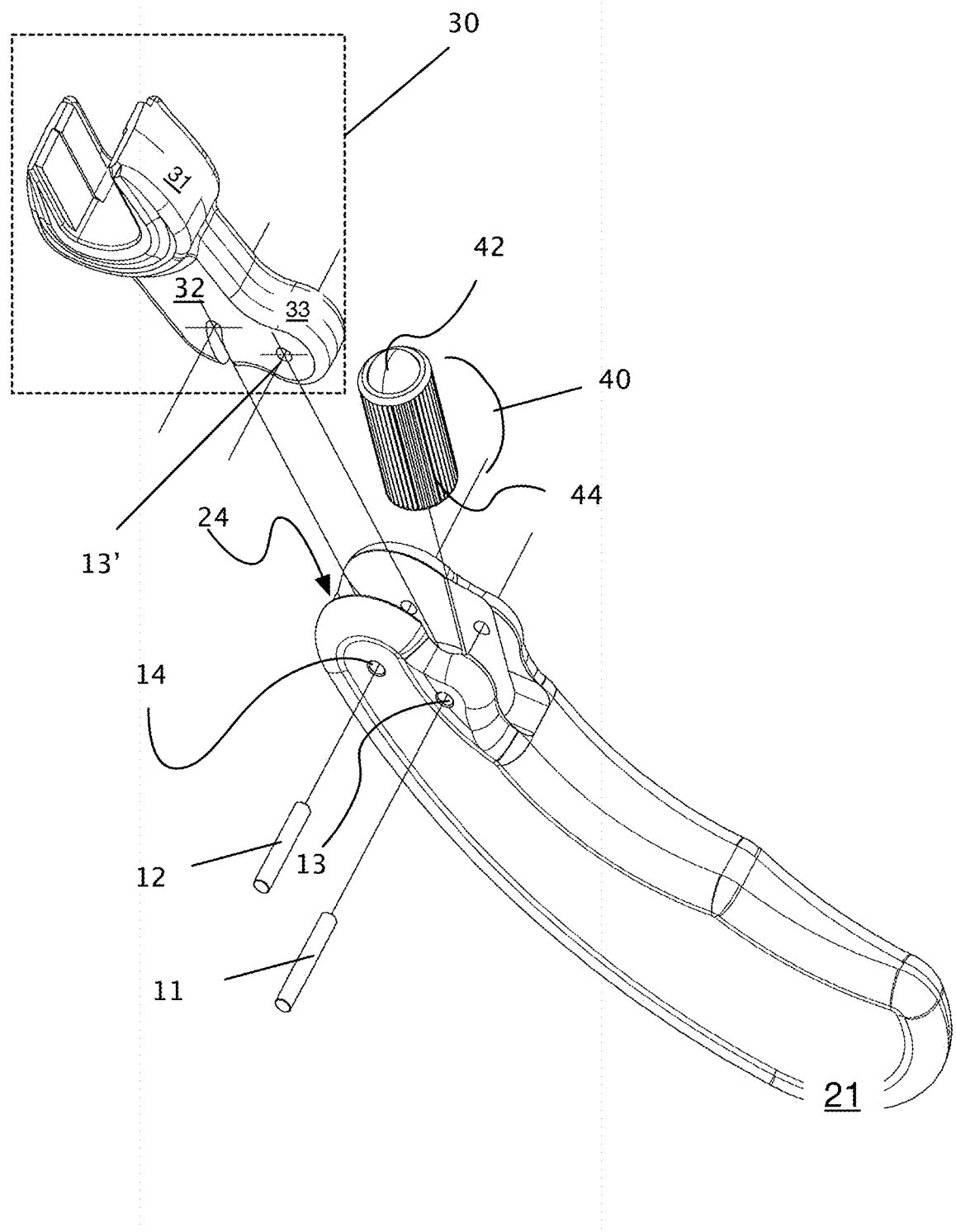
FIG. 2A shows aspects of the assembly of an asymmetrical disposable torque limiting device with spring actuator.
Figure 2B:
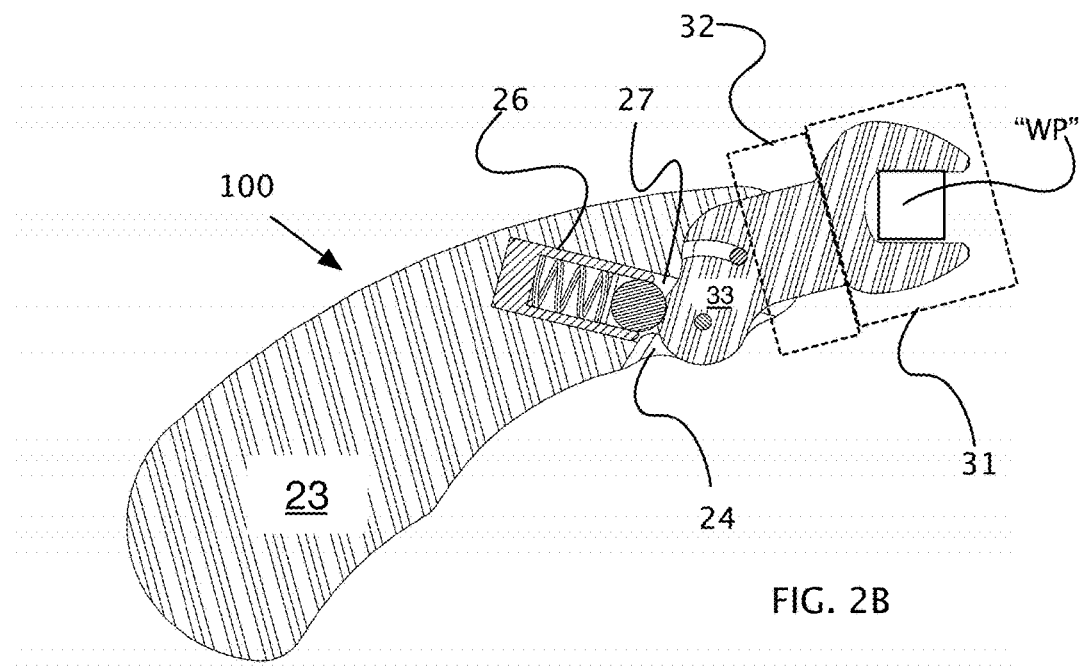
FIGS. 2B and 2C show aspects of a cutaway and exploded partial cut away of the unactuated asymmetrical disposable torque limiting device of FIG. 2A.
Figure 2C:
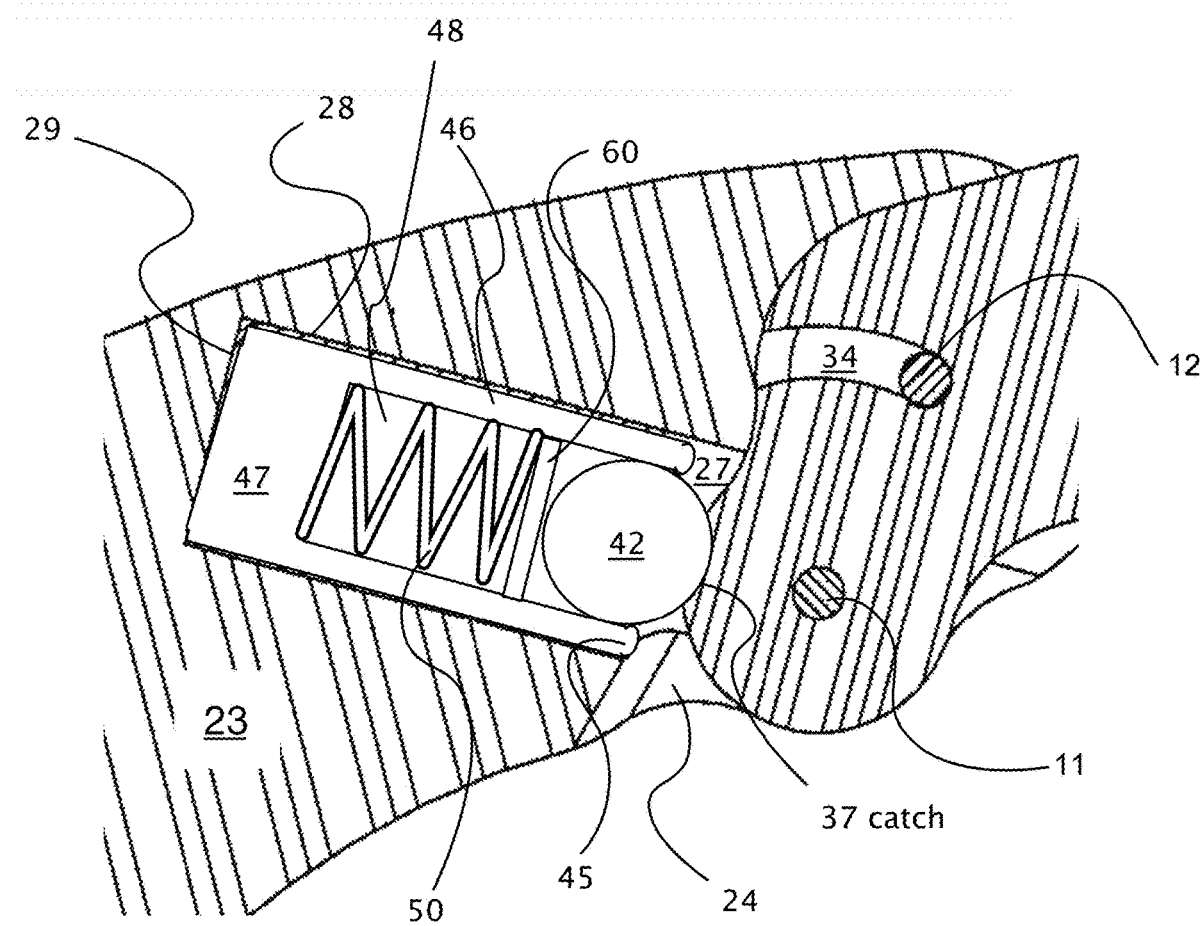

FIGS. 1A through 1C provide external views of an asymmetrical disposable torque limiting device (ADTLD) 10 which may also be referred to as a disposable asymmetrical torque limiting system (DATLS) wherein the tool portions may be swapped out and changed on demand. FIG. 2A illustrates assembly of an ADTLD or DATLS with an internal actuation means. FIG. 1A shows the unactuated configuration and FIG. 1C shows a fully actuated configuration. Fully actuated means that the tool portion is disengaged from the force providing means within the device or system. FIG. 1C illustrates a unidirectional tool portion 30 of a DATLS.

The system and/or device 10 has a handle portion 20 with an attached tool portion 30. The tool portion can be further broken down into a work piece tool portion 31 connected by a neck 32 to a body 33 which mates in a movable (and in some cases removable) fashion to the handle. The handle may be a two half component whereby two mirror each with an exterior surface 21 and an interior surface 23 mate to form a handle to mate a tool portion to. The handle has a back side 22' and a front side 22.

The tool portion is movably mounted to the handle in a tool containment 24 interface formed on the front side 22 of the handle (thereby making the device asymmetrical as the interface supports a one sided movement of the tool portion) via first retention pin 11 which mates with a first pin guide 13 in the handle (formed through both side walls on either side of the handle) and with a second pin guide 13' in the tool. The first retention pin and first pin guide are configured so that the pin fits snugly in that guide. A second pin guide is configured to allow the tool to rotate about the first retention pin. Optionally, a second retention pin 12 within the tool containment 24 fits snugly into an optional third pin guide 14 in the handle. The body 33 of the tool may optionally include a guide slot 34 is configured to accept the second retention pin without biding against it. The pin should move freely within the guide during rotational movement of the tool along the path of arrow 1000. If the second retention pin is not included in the retention system such a slot is not necessary.

The tool may optionally have the work piece tool head portion configured non-homogeneously with a first work piece interface 35 and a second workpiece interface 36. Wherein the each work piece interface is a subset of the workpiece engaging region "WER". Via the interfaces the tool head portion can only accept a workpiece in one direction. Unidirectional acceptance of a workpiece is important if the tool is to be used to provide a pre-determined amount of torque in a particular rotational direction. If the tool was reversible a user may inadvertently apply the force in the counter direction. By making the head portion unidirectional to mate only one way with a work piece such mistakes can be avoided.

FIGS. 2A-5B illustrate aspects of the handle configured with an actuator containment 26 having an open end 27 an annular wall 28 and a closed end 29. The containment has a known diameter.

FIGS. 2A-3B show aspects of exemplars with a spring actuator engine (SAE) 40. The SAE is generally cylindrical with a ball 42 fitted into the open end 45 of the closed cylinder engine housing 44 which has an annular wall 46 surrounding a spring 50 and an end portion 47 closing off the cylinder. The cylinder engine housing and volume 48 therein is configured to accept the diameter of the ball 42 therein. The open end 45 is configured to prevent the ball from being ejected by the force of the spring when the device is actuated. The ball partially extends out of the actuator to form a movable interface with the tool portion configured to provide torque limiting functionality. Those of ordinary skill in the art will understand that prevention to include but not be limited to crimping the open end, making the open end a smaller diameter than the ball yet elastic enough to press fit the ball therein with force exceeding that of the spring. A spring shield 60 may be added to evenly spread the force of the coil spring 50 against the ball 42. The spring shield is shown flat but optionally may be concave to better fit the ball. The spring shield is configured to move freely along an axial path within the volume 48 of the engine housing formed by the annular wall 48 At least one of the spring, end portion 47 and spring shield 60 are configured to provide a predetermined amount of force resisting the movement of the ball into the cylinder engine housing 44. FIG. 2D illustrates the tool portion 30 in the actuated position after sufficient rotational force has been applied to the tool portion 30 to cause it to overcome the retaining force of the ball against a body catch 37 whereby the tool portion rotates about the first retention pin and limits the torque applied the an engaged workpiece (not shown). In the above exemplars the spring is selected to have a predetermined compressive force limit for the SAE thereby fixing a narrow range of torque limit to the device. The body catch forms an interface to cooperate with the ball shape to hold the tool portion in place until such time as the force applied overcomes the resistance of the actuator. The method includes steps of disengaging the tool portion body catch from the ball or ball shaped end when the system or device has sufficient torque applied to the tool portion, said tool portion will rotate and disengage. That disengagement may also be referred to as the device being actuated. An unactuated device refers to a device or system wherein the tool portion has not overcome the torque limits and may continue to be used to engage a workpiece "WP" via the workpiece engaging region "WER". Those of ordinary skill in the art will recognize that the body catch 37 is a catch which corresponds to a latch and the two features cooperate to form a temporary latch—catch which holds until sufficient force is applied to overcome the resistance of the component applying force to the catch. The catch should generally be configured to correspond to the ball or lever or other latch which cooperates therewith and that the plethora of such cooperating structures are within the scope of this disclosure.

Aspects methods include placing an actuator in a tool containment interface of a handle and movable mounting the tool portion with an actuation catch and a work piece engaging region in the interface; the method applies sufficient force to the tool portion to allow a user to apply torque at a set limit to a workpiece until such time as the actuator is disengaged.

FIGS. 3A and 3B show an alternate exemplary 150 wherein the tool portion is removable. Specifically, a modified tool portion 30' replaces the second pin guide 13' with a retention slot 155 whereby the tool portion is temporarily held in the system and fully removable. Once the torque limits are met the tool portion may be rotated (along the line of arrow 1005) out of the tool containment 24 for disposal, replacement or to be swapped.

FIGS. 4A-4C illustrated an exemplary system and device wherein SAE is replaced by a lever actuate engine (LAE) 210 and the body 33 of the tool portion 30 is configured with a lever catch 212 instead of a ball catch. The LAE has a body 215 which fits into the containment 26 and a flexible force lever 220 which requires a predetermined amount of force to be applied to it to bend and allow the lever catch to pass by it during rotation of the tool portion. The force lever is frangible and it will one of break and bend beyond the memory of the material and become dysfunctional post actuation. Rotation along the line of arrow 1010 results in the non-functional force lever post actuation.

Figure 5A:
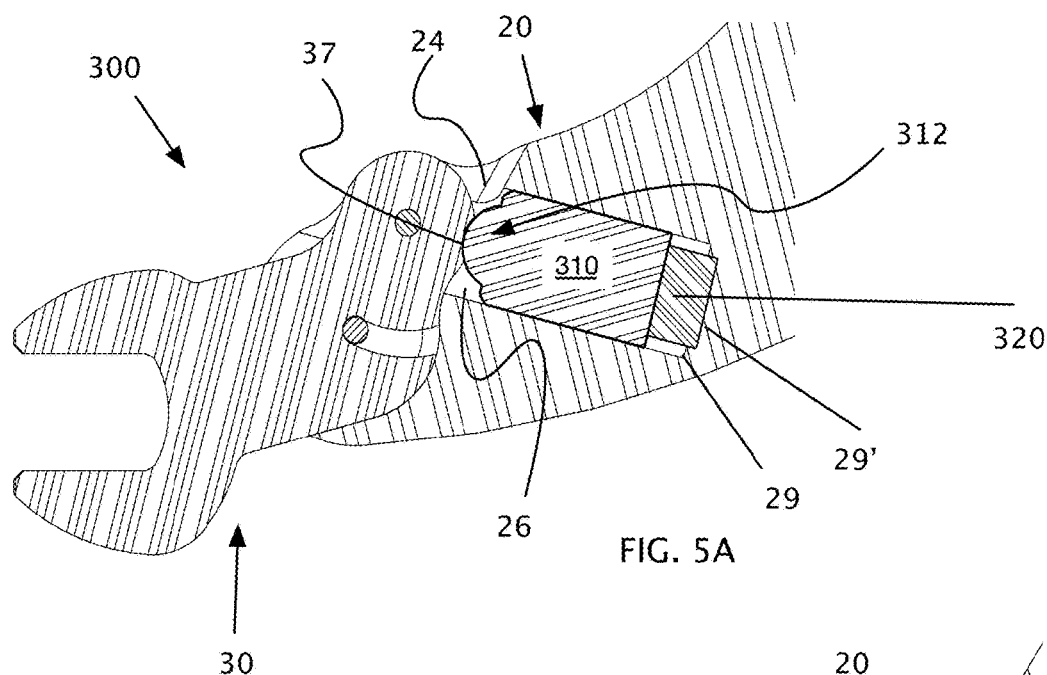
FIGS. 5A and 5B show an asymmetrical disposable torque limiting device with bushing actuator configured to set a predetermined torque limit.
Figure 5B:
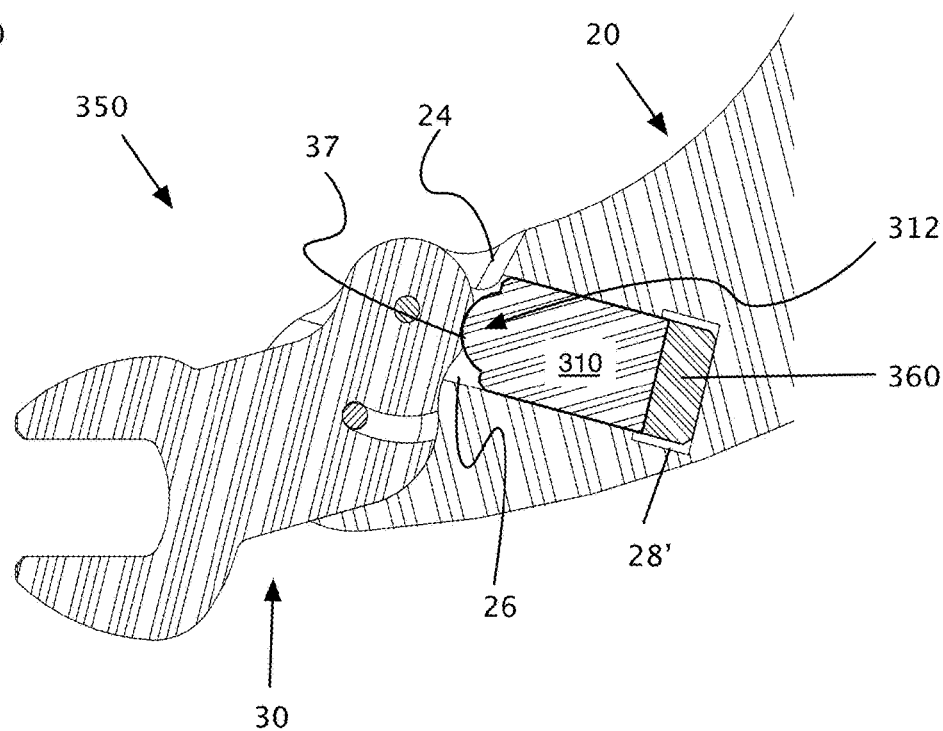

FIGS. 5A-5B illustrate an exemplary system and device wherein SAE is replaced by a bushing actuate engine (BAE). In FIG. 5A the bushing engine BAE is a two part configuration with an actuation body 310 and an elastomeric bushing 320 configured to cause the ball 312 shaped nose of the actuation body to apply a predetermined amount of force to the body catch 37. The closed end 29 of the containment 26 has a bushing well 29' with a smaller diameter than the containment and configured to retain an elastomeric bushing 320 central in the containment and allowing volume around the bushing for expansion which will occur during compression by the application of force to the nose 312.

In FIG. 5B the bushing actuation engine (BAE) is a two part configuration with an actuation body 310 and a elastomeric bushing 360 configured to cause the ball 312 shaped nose of the actuation body to apply a predetermined amount of force to the body catch. The annular wall 28 of the containment 26 has a bushing expansion region 28' which is of a greater diameter than the containment to allow volume around the bushing for bushing expansion which will occur during compression by the application of force to the nose 312. In either of the above exemplars the bushing is selected to provide a predetermined force limit to the engine thereby fixing a narrow range of torque limit to the device.

Figure 6:
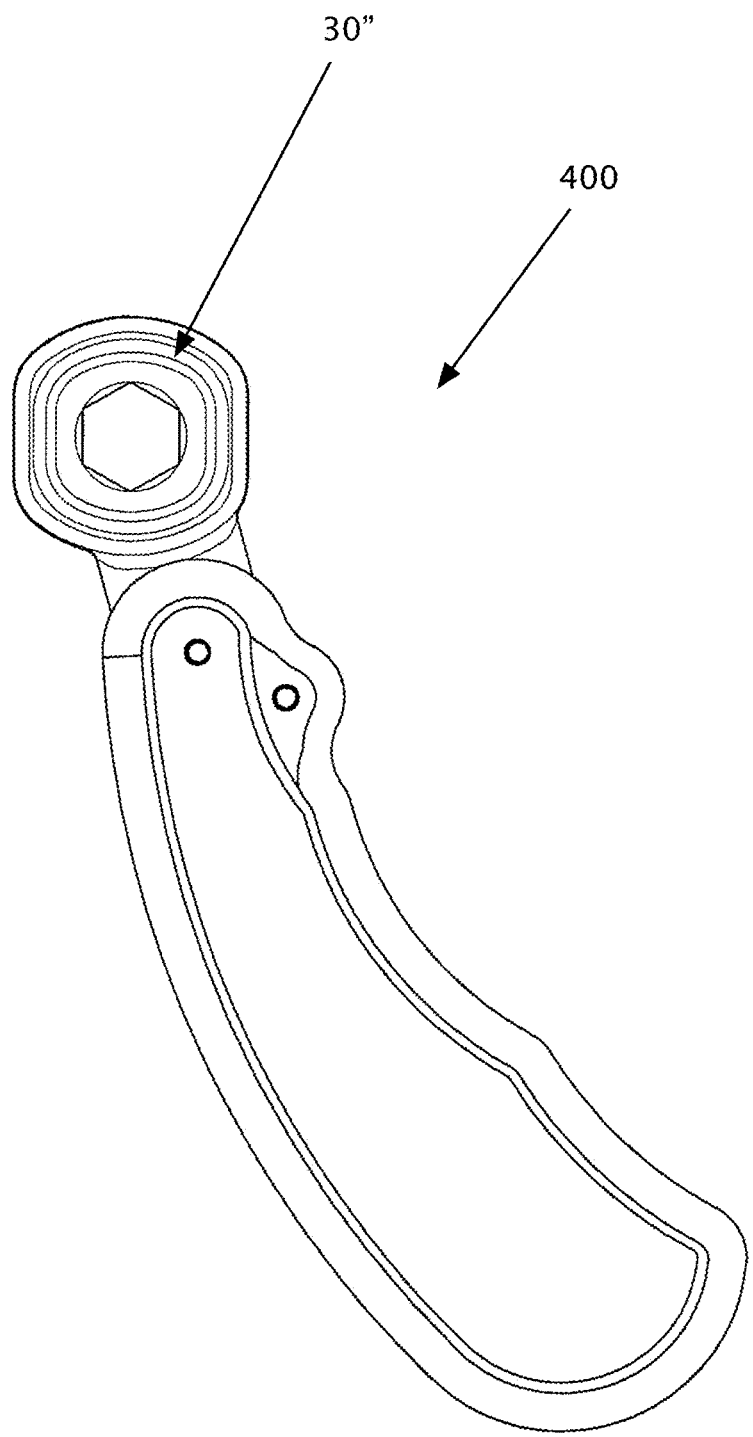
FIG. 6 shows aspects of an asymmetrical disposable torque limiting device.

FIG. 6 illustrates aspects of an asymmetrical disposable torque limiting device 400 with a close ended WER 410.

FIG. 7A shows a top view of an asymmetrical disposable torque limiting device:

FIG. 7B shows a left side view of an asymmetrical disposable torque limiting device.

FIG. 7C shows a bottom view of an asymmetrical disposable torque limiting device.

FIG. 7D shows a right side view of an asymmetrical disposable torque limiting device.

FIG. 7E shows a front side view of an asymmetrical disposable torque limiting device.

FIG. 7F shows a back side view of an asymmetrical disposable torque limiting device.

Figure 8:
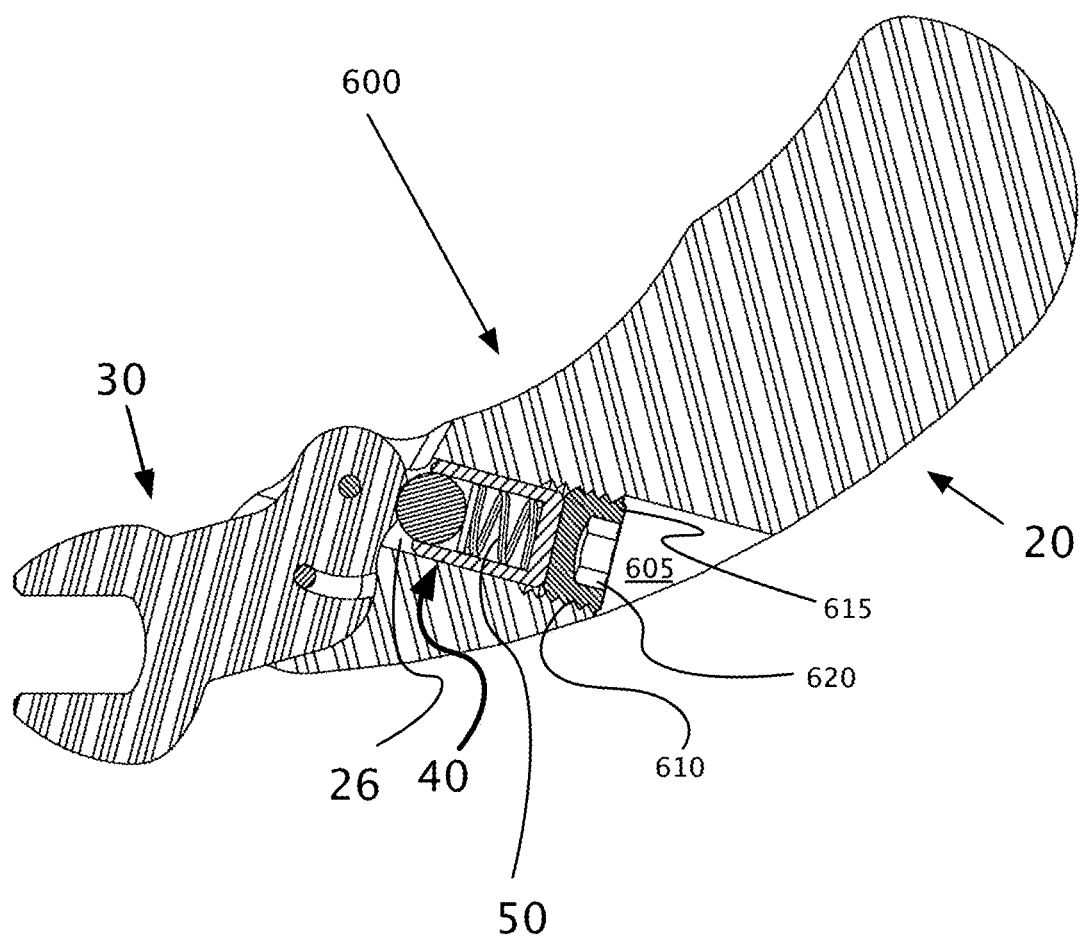
FIG. 8 shows a cut-away presenting aspects of an adjustable side view of an asymmetrical disposable torque limiting device.

FIG. 8 shows a cut-away presenting aspects of an adjustable side view of an asymmetrical disposable torque limiting device 600. An adjustment interface 605 provides a threaded 610 channel which is fluidly connected to the containment 26. A threaded fixation fastener 615 configured to cooperatively mount in the threaded 610 channel. The fastener having an adjustment mount 620 shown as a mating region for a hex wrench or screw driver is provided. The fastener is used to adjust the depth of the actuation means 40 within the containment relative to the tool portion. The depth adjustment of the adjustment fastener is used to increase or decrease the force applied by the spring 50 in this case to the tool portion at the catch 37. In other instances such as the exemplars is FIG. 5A or 5B utilizing bushings, the adjustment fastener works in the same fashion as described in reference to FIG. 8.

Figure 9:
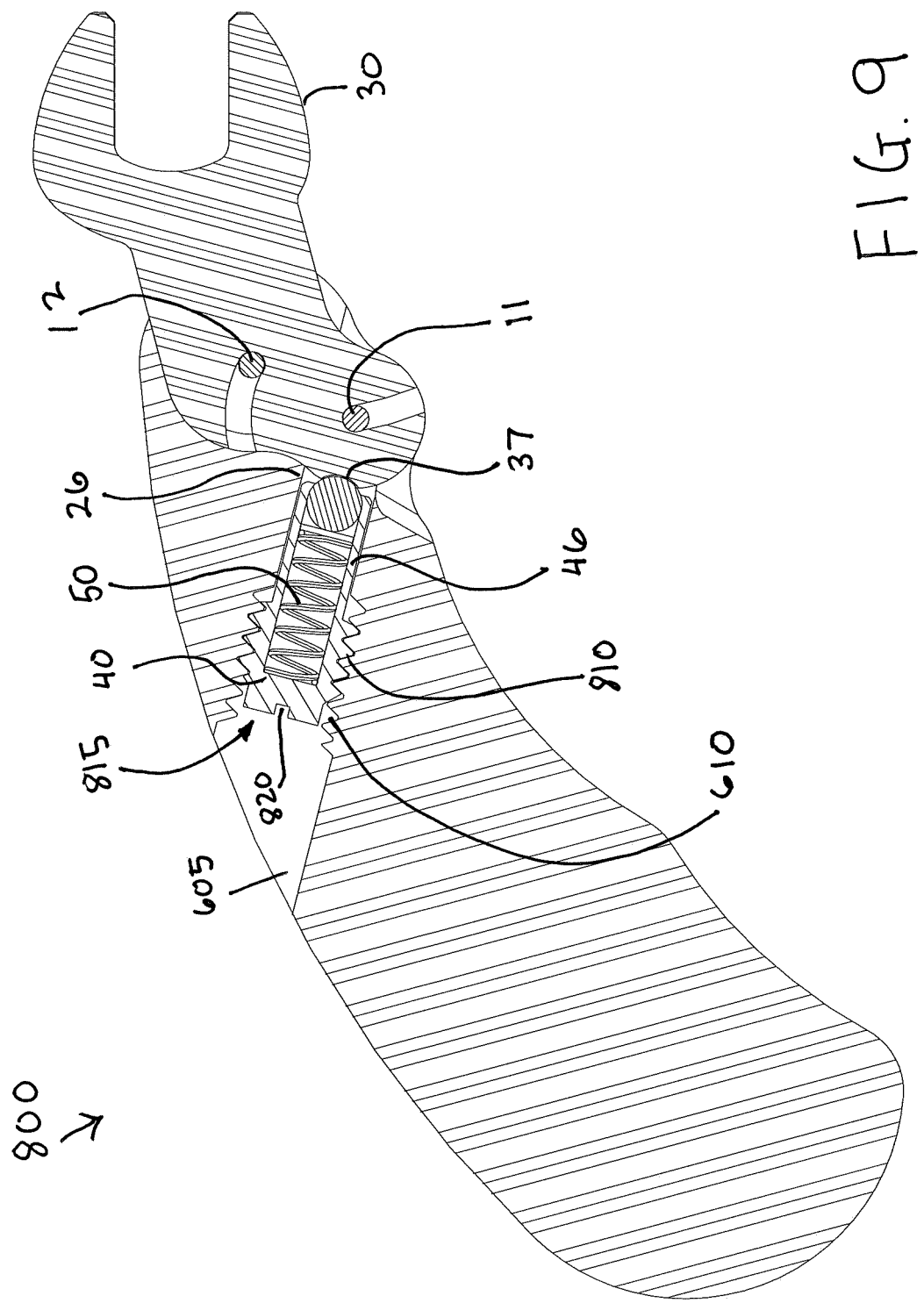
FIG. 9 shows a cut-away presenting aspects of an adjustable side view of an asymmetrical disposable torque limiting device with adjustable containment.

FIG. 9 shows a cut-away presenting aspects of an adjustable side view of an asymmetrical disposable torque limiting device 800. An adjustment interface 605 provides a threaded 610 channel which is fluidly connected to the containment 26. The SAE 40 engine housing has an annular wall 46 which is at least partially threaded 810 to cooperatively mount in the threaded 610 channel. The SAE also provides an adjustment interface 815 which is accessed through an adjustment mount 820 shown as a mating region for a hex wrench or screw driver. The fastener is used to adjust the depth of the SAE within the containment relative to the tool portion. The depth adjustment is used to increase or decrease the force applied by the spring 50, in this case, to the tool portion at the catch 37.

Those of ordinary skill in the art will recognize that the threaded 610 channel and threaded fastener 615 may be replaced with a fastener that connects to the interface 605 in a plethora of ways. Including but not limited to pressure fit, adhesive, sonic weld, a threaded fastener harder than the cannel material that creates its own cooperating groves as it is mounted that forms its own.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. An adjustable disposable torque limiting device comprising:
   a handle with a tool containment interface;
   a first pin guide and a third pin guide formed through said handle;
   said tool containment configured with a closed end formed in said handle;
   an actuator with a movable ball end mounted in said containment; an adjustment interface connected to said containment;
   a tool portion configured to movably fit in at least part of said tool containment comprising:
      a work piece engaging region;
      a retention slot formed in said tool portion;
      a guide slot formed in said tool portion; and
      a body catch forming an interface for said movable ball end of said actuator;
   a first pin configured to fit through said first pin guide and move along in said retention slot in said tool portion during rotational movement of said tool portion;
   a second pin configured to fit through said third guide and move along said guide slot in said tool portion during rotational movement of said tool portion;
   wherein said tool portion may be removed from said tool containment by rotating it off of said first and second pins;
   a fixation fastener configured to mount in said adjustment interface;
   wherein when sufficient force is applied to said actuator said body catch disengages said movable ball end and said tool portion is released.

2. The adjustable disposable torque limiting device of claim 1,
   wherein said adjustment interface has a threaded portion; and, said fixation fastener is threaded.

3. The adjustable disposable torque limiting device of claim 2, said actuator further comprising a generally cylindrical housing with an open end and an end portion closing off said cylindrical housing;
   a spring resting against said end portion; and, said moveable ball end comprising a ball fitted into said housing and extending into said body catch.

4. The adjustable disposable torque limiting device of claim 3, wherein said spring has a predetermined compressive force limit.

5. The adjustable disposable torque limiting device of claim 2, said actuator further comprising an actuation body and an elastomeric bushing configured to cause said movable ball end of said actuation body to apply a predetermined amount of force to said body catch.

6. The adjustable disposable torque limiting device of claim 5, wherein said bushing has a diameter less than the diameter inside said containment.

7. The adjustable disposable torque limiting device of claim 6, wherein said bushing fits into a well configured to retain said bushing and allowing volume around said bushing for expansion which will occur during compression by the application of force to said movable ball end.

8. The adjustable disposable torque limiting device of claim 2, said actuator further comprising an actuation body and a elastomeric bushing configured to cause said movable ball end of said actuation body to apply a predetermined amount of force to said body catch.

9. The adjustable disposable torque limiting device of claim 8, wherein said containment is an annular wall, and said containment has a bushing expansion region of said annular wall which is of a greater diameter inside said containment to allow volume around said bushing for bushing expansion which will occur during compression by the application of force to said movable ball end.

10. An adjustable disposable torque limiting device comprising:
    a handle with a tool containment interface formed on a side of said handle that is opposite of a side of said handle configured to be held;
    a fiist pin guide and a third pin guide formed through said handle;
    said tool containment interface comprising an annular wall and a closed end formed in said handle;
    an actuator with a force lever mounted in said tool containment interface, wherein said force lever is configured to be frangible;
    a tool portion configured to movably fit in at least part of said tool containment interface comprising:
       a work piece engaging region;
       a second pin guide formed in said tool portion;
       a guide slot formed in said tool portion; and
       a lever catch forming an interface with said force lever;
    a first pin configured to fit through said first pin guide in said handle and said second pin guide in said tool portion so as to connect said handle to said tool portion;
    a second pin configured to fit, through said third guide and move along said guide slot in said tool portion during rotational movement of said tool portion;
    a fixation fastener configured to mount in an adjustment interface; and,
    wherein when sufficient force is applied to said actuator, said lever catch disengages said force lever from said lever catch and the said portion is released from torque limiting provided by said actuator.

* * * * *